(12) United States Patent
Abboud et al.

(10) Patent No.: US 8,383,614 B2
(45) Date of Patent: Feb. 26, 2013

(54) HYPERCHOLESTROLEMIA AND TENDINOUS INJURIES

(75) Inventors: Joseph A. Abboud, Bryn Mawr, PA (US); Louis J. Soslowsky, Penn Valley, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/359,695

(22) Filed: Jan. 26, 2009

(65) Prior Publication Data

US 2009/0197858 A1 Aug. 6, 2009

Related U.S. Application Data

(60) Provisional application No. 61/006,804, filed on Jan. 31, 2008.

(51) Int. Cl.
| | |
|---|---|
| *A61K 31/397* | (2006.01) |
| *A61K 31/40* | (2006.01) |
| *A61K 31/435* | (2006.01) |
| *A61K 31/404* | (2006.01) |
| *A61K 31/366* | (2006.01) |
| *A61K 31/47* | (2006.01) |
| *A61K 31/505* | (2006.01) |
| *A61K 31/351* | (2006.01) |
| *A61P 21/00* | (2006.01) |
| *C12Q 1/60* | (2006.01) |

(52) U.S. Cl. ............... 514/210.02; 514/423; 514/277; 514/419; 514/460; 514/311; 514/275; 435/11

(58) Field of Classification Search ............ 514/210.02, 514/423, 277, 419, 460, 311, 275; 435/11
See application file for complete search history.

(56) References Cited

U.S. PATENT DOCUMENTS

| | | | | |
|---|---|---|---|---|
| 6,858,618 B2 * | 2/2005 | Raza et al. | ..................... | 514/275 |
| 2002/0156122 A1 * | 10/2002 | Mach | ............................ | 514/423 |
| 2005/0026979 A1 * | 2/2005 | Ghazzi et al. | ................. | 514/381 |
| 2009/0159193 A1 * | 6/2009 | Leykamm | .................... | 156/256 |

* cited by examiner

*Primary Examiner* — San-Ming Hui
*Assistant Examiner* — Kathrien Cruz
(74) *Attorney, Agent, or Firm* — Mark S. Cohen; Pearl Cohen Zedek Latzer, LLP

(57) ABSTRACT

This invention provides compositions and methods of inhibiting, suppressing, or treating a tendinous or musculoskeletal soft tissue injury. The invention further provides a method of ameliorating symptoms associated with a tendinous or musculoskeletal soft tissue injury. Additionally, the invention provides methods for evaluating the risk of developing a tendinous or musculoskeletal soft tissue injury.

12 Claims, 7 Drawing Sheets

A

B

HYPERCHOLESTROLEMIA AND TENDINOUS INJURIES

CROSS REFERENCE TO RELATED APPLICATIONS

This application claims priority to U.S. Provisional Patent Application No. 61/006,804, filed Jan. 31, 2008, which is hereby incorporated by reference in its entirety.

FIELD OF INVENTION

The invention relates to compositions and methods for treating and detecting a tendinous injury. Specifically, the invention relates to administering a cholesterol lowering agent to treat a tendinous injury.

BACKGROUND OF THE INVENTION

Musculoskeletal soft tissue injuries from athletic activities are common in the rotator cuff tendons, lateral epicondyle of the elbow, the patella tendon, and the achilles tendon. Despite the fact that the achilles tendon is the largest and strongest tendon in the human body, it is frequently injured in the athletic setting.

Achilles tendon injuries range from inflammation of the paratendinous tissue, to structural degeneration of the tendon (tendinosis), and finally, to tendon rupture. The most common clinical presentation of achilles tendon injuries is tendinopathy. It is characterized by a combination of pain and swelling in the achilles tendon accompanied by impaired ability to participate in strenuous activity. Many achilles tendon ruptures occur without precipitating signs and symptoms and it is widely accepted that surgical repair should be performed in physically active patients. To better prevent and treat injuries to the Achilles tendon, it is necessary to understand the etiology and pathogenesis of the disease process.

Intrinsic, extrinsic, and overuse activity are well-known factors responsible for tendinous injuries in general. Previous studies on the achilles tendon were often from a surgical reconstructive or clinical retrospective standpoint. While important, these studies were not designed to determine the roles of disease etiology and pathogenesis. Accordingly, a need exists to determine the roles of disease etiology and pathogenesis, and thereby develop improved compositions and methods for treating tendinous injuries.

SUMMARY OF THE INVENTION

In one embodiment, the invention provides a method of treating a tendinous or musculoskeletal soft tissue injury, in a subject, comprising administering to said subject a cholesterol lowering agent, wherein said cholesterol lowering agent inhibits or reverses tendon xanthomata, thereby treating said tendinous or musculoskeletal soft tissue injury in said subject.

In another embodiment, the invention provides a method of inhibiting or suppressing a tendinous or musculoskeletal soft tissue injury, in a subject, comprising the step of: administering to said subject a cholesterol lowering agent, wherein said cholesterol lowering agent inhibits or reverses tendon xanthomata, thereby inhibiting or suppressing said tendinous or musculoskeletal soft tissue injury in said subject.

In another embodiment, the invention provides a method of ameliorating symptoms associated with a tendinous or musculoskeletal soft tissue injury, in a subject, comprising the step of: administering to said subject a cholesterol lowering agent wherein said cholesterol lowering agent inhibits or reverses tendon xanthomata, thereby ameliorating symptoms associated with said tendinous or musculoskeletal soft tissue injury in said subject.

In another embodiment, the invention provides a method of accelerating the healing of a tendinous or musculoskeletal soft tissue injury, in a subject, comprising the step of: administering to said subject a cholesterol lowering agent, wherein said cholesterol lowering agent inhibits or reverses tendon xanthomata, thereby accelerating the healing of said tendinous or musculoskeletal soft tissue injury in said subject.

In another embodiment, the invention provides a method of preserving a biomechanical property of a tendon in a subject, comprising administering to said subject a cholesterol lowering agent, thereby preserving a biomechanical property of a tendon in said subject.

In another embodiment, the invention provides a method of evaluating the risk of developing a tendinous or musculoskeletal soft tissue injury, in a subject, comprising the steps of: obtaining a biological sample from a subject; analyzing the concentration of TC, HDL-C, LDL-C, TG or their combination; and comparing the concentration to a standard, whereby if the concentration of TC, HDL-C, LDL-C, TG or their combination is different than the concentration of said standard, the subject is in high risk of developing a tendinous or musculoskeletal soft tissue injury.

In another embodiment, the present invention provides a kit for diagnosing the risk of developing a tendinous or musculoskeletal soft tissue injury in a subject, comprising reagents, packaging and instructions for analyzing the concentration of TC, HDL-C, LDL-C, TG or their combination in a biological sample of the subject.

In another embodiment, the invention provides a pharmaceutical composition for treating a tendinous or musculoskeletal soft tissue injury, in a subject, comprising a therapeutically effective amount of a cholesterol lowering agent, wherein said therapeutically effective amount of said cholesterol lowering agent inhibits or reverses tendon xanthomata, thereby treating said tendinous or musculoskeletal soft tissue injury in said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The application file contains drawings executed in color. Copies of this patent or patent application with color drawings will be provided by the Office upon request and payment of the necessary fee.

DETAILED DESCRIPTION OF THE INVENTION

Figure 1:
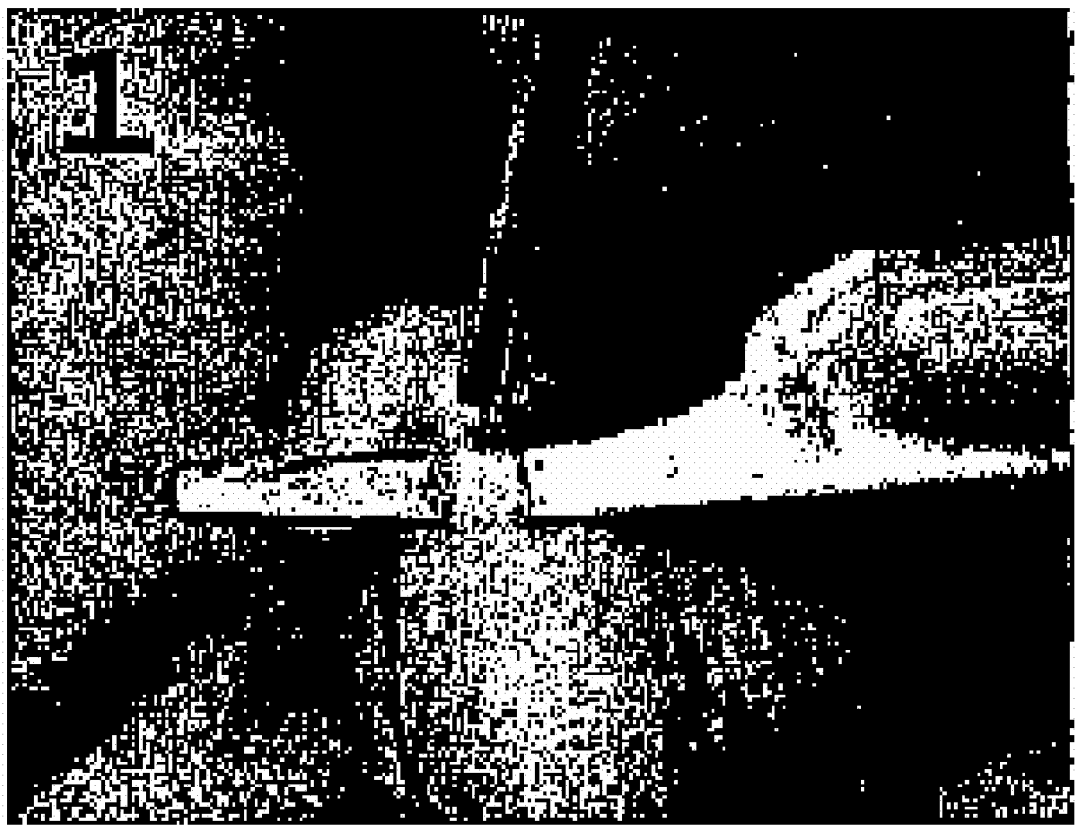
FIG. 1 is a photograph showing the circular punch that creates a partial transection in the middle half of the mouse patellar tendon.

The invention relates to compositions and methods for treating and detecting a tendinous injury. In particular, the invention relates to administering a cholesterol lowering agent to treat a tendinous injury.

In one embodiment, the invention provides a method of treating a subject afflicted with a tendinous or musculoskeletal soft tissue injury. The method comprises administering to a subject a cholesterol lowering agent. In some embodiments, the cholesterol lowering agent inhibits or reverses tendon xanthomata, thereby treats a tendinous or musculoskeletal soft tissue injury.

In one embodiment, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a subject in contact with an agent of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject. The term "subject," as used herein, includes any human or non-human animal. The term "non-human animal" includes all vertebrates, e.g., mammals and non-mammals.

In one embodiment, the cholesterol lowering agent is a HMG-CoA reductase inhibitor. In another embodiment, the cholesterol lowering agent increases the clearance of low-density lipoprotein (LDL) from the bloodstream.

In one embodiment, the cholesterol lowering agent of the invention is a statin. In another embodiment, the cholesterol lowering agent is atorvastatin. In another embodiment, the cholesterol lowering agent is cerivastatin. In another embodiment, the cholesterol lowering agent is lovastatin. In another embodiment, the cholesterol lowering agent is mevastatin. In another embodiment, the cholesterol lowering agent is fluvastatin. In another embodiment, the cholesterol lowering agent is pitavastatin. In another embodiment, the cholesterol lowering agent is pravastatin. In another embodiment, the cholesterol lowering agent is rosuvastatin. In another embodiment, the cholesterol lowering agent is simvastatin. In another embodiment, the cholesterol lowering agent is any combination of statins. In another embodiment, the cholesterol lowering agent is ezetimibe. In another embodiment, the present invention provides that the cholesterol lowering composition comprises simvastatin and ezetimibe. In another embodiment, the present invention provides that the cholesterol lowering composition comprises lovastatin and niacin. In another embodiment, the present invention provides that the cholesterol lowering composition comprises atorvastatin and amlodipine.

In another embodiment, the present invention provides that cholesterol comprises low-density lipoprotein (LDL). In another embodiment, the present invention provides that cholesterol comprises high-density lipoprotein (HDL).

In another embodiment, the present invention provides that hypercholesterolemia is blood cholesterol concentration greater than or equal to 240 mg/dL. In another embodiment, the present invention provides that hypercholesterolemia is blood cholesterol concentration greater than or equal to 220 mg/dL. In another embodiment, the present invention provides that hypercholesterolemia is blood cholesterol concentration greater than 200 mg/dL.

In another embodiment, the present invention provides that the cholesterol lowering agent lowers a subject blood total cholesterol concentration below about 240 mg/dL. In another embodiment, the present invention provides that the cholesterol lowering agent lowers a subject blood total cholesterol concentration below about 220 mg/dL. In another embodiment, the present invention provides that the cholesterol lowering agent lowers a subject blood total cholesterol concentration below about 200 mg/dL.

In another embodiment, the present invention provides that the cholesterol lowering agent lowers a subject blood total Low-density lipoprotein-C (LDL) to below about 130 mg/DL. In another embodiment, the present invention provides that the cholesterol lowering agent lowers a subject blood total LDL-C to below about 120 mg/DL. In another embodiment, the present invention provides that the cholesterol lowering agent lowers a subject blood total LDL-C to below about 110 mg/DL. In another embodiment, the present invention provides that the cholesterol lowering agent lowers a subject blood total LDL-C to below about 100 mg/DL.

In another embodiment, the present invention provides that the cholesterol lowering agent lowers a subject blood total High-density lipoprotein-C (HDL) to above about 40 mg/DL. In another embodiment, the present invention provides that the cholesterol lowering agent lowers a subject blood total HDL-C to above about 45 mg/DL. In another embodiment, the present invention provides that the cholesterol lowering agent lowers a subject blood total HDL-C to above about 50 mg/DL. In another embodiment, the present invention provides that the cholesterol lowering agent lowers a subject blood total HDL-C to above about 55 mg/DL. In another embodiment, the present invention provides that the cholesterol lowering agent lowers a subject blood total HDL-C to above about 60 mg/DL.

In another embodiment, the present invention provides that the cholesterol lowering agent lowers a subject blood total triglycerides (TG) to below about 150 mg/DL. In another embodiment, the present invention provides that the cholesterol lowering agent lowers a subject blood total TG to below about 140 mg/DL. In another embodiment, the present invention provides that the cholesterol lowering agent lowers a subject blood total TG to below about 130 mg/DL. In another embodiment, the present invention provides that the cholesterol lowering agent lowers a subject blood total TG to below about 120 mg/DL.

In another embodiment, the present invention provides that the cholesterol lowering agent lowers a subject blood total cholesterol concentration below about 240 mg/dL, LDL-C to below about 130 mg/DL, HDL-C to below above about 40 mg/DL, TG to below about 150 mg/DL, or their combination. In another embodiment, the present invention provides that the cholesterol lowering agent lowers a subject blood total cholesterol concentration below about 240 mg/dL, LDL-C to below about 130 mg/DL, HDL-C to below above about 40 mg/DL, TG to below about 150 mg/DL, or their ratio.

In another embodiment, the present invention provides that tendon injuries comprise chronic degenerative changes.

In another embodiment, the present invention provides that the tendinous injury is a rotator cuff injury. In another embodiment, the present invention provides that the tendinous injury is an elbow-tendon injury. In another embodiment, the present invention provides that the tendinous injury is a rotator cuff injury and an elbow-tendon injury. In another embodiment, the present invention provides that the tendinous injury is tennis elbow (lateral epicondylitis). In another embodiment, the present invention provides that the tendinous injury is golfer's elbow (medial epicondylitis). In another embodiment, the present invention provides that the tendinous injury is flexor tendonitis. In another embodiment, the present invention provides that the tendinous injury is extensor tendonitis. In another embodiment, the present invention provides that the tendinous injury is peroneal tendonitis. In another embodiment, the present invention provides that the tendinous injury is achilles tendinitis. In another embodiment, the present invention provides that the tendinous injury is rotator cuff tendinitis. In another embodiment, the present invention provides that the tendinous injury is patellar (kneecap) tendinitis. In another embodiment, the present invention provides that the tendinous injury is wrist tendinitis. In another embodiment, the present invention provides that the tendinous injury is tendinitis (and overuse injuries) in children. In another embodiment, the present invention provides that the tendinous injury is carpal tunnel syndrome. In another embodiment, the present invention provides that the tendinous injury is tendinitis (ruptured tendons) of the knee.

In another embodiment, the present invention provides that the tendinous injury is tendinopathy. In another embodiment, the present invention provides that the tendinous injury is characterized by a painful or torn tendon. In another embodiment, the present invention provides that the tendinous injury comprises a series of microtears in the connective tissue or around the tendon. In another embodiment, the present invention provides that the tendinous injury is tendinosis.

In another embodiment, the present invention provides that musculoskeletal soft tissue injury and/or tendon injury is associated with disorders such as osteoarthritis, rheumatoid arthritis, carpal tunnel syndrome, and tendinitis. In another embodiment, the present invention provides that cholesterol lowering agent is used to treat, prevent, or reduce the symptoms associated with a musculoskeletal soft tissue injury and/or a tendon injury, wherein the musculoskeletal soft tissue injury and/or tendon injury is associated with disorders such as osteoarthritis, rheumatoid arthritis, carpal tunnel syndrome, and tendinitis. In another embodiment, the present invention provides that a statin is used to treat, prevent, or reduce the symptoms associated with a musculoskeletal soft tissue injury and/or a tendon injury, wherein the musculoskeletal soft tissue injury and/or tendon injury is associated with disorders such as osteoarthritis, rheumatoid arthritis, carpal tunnel syndrome, and tendinitis.

In another embodiment, methods of the present invention further comprise treating inflammation associated with a tendinous injury or a musculoskeletal soft tissue injury. In another embodiment, methods of treating inflammation associated with a tendinous injury or a musculoskeletal soft tissue injury are known to one of skill in the art.

In another embodiment, methods of the present further comprise treating edema associated associated with a tendinous injury or a musculoskeletal soft tissue injury. In another embodiment, methods of treating edema associated with a tendinous injury or a musculoskeletal soft tissue injury are known to one of skill in the art.

In another embodiment, the present invention provides that a tendon injury usually can be diagnosed with a review of medical history and recent activities and a physical examination. In another embodiment, the present invention provides that treatment progress is monitored by periodic assessment of tendon/ligament-like tissue formation, or tendon or ligament growth and/or repair. The progress can be monitored by methods known in the art, for example, X-rays, arthroscopy, histomorphometric determinations, ultrasound, magnetic resonance image (MRI) and tetracycline labeling.

In another embodiment, the present invention provides a method of inhibiting or suppressing a tendinous or a musculoskeletal soft tissue injury in a subject, comprising the step of: administering to a subject a cholesterol lowering agent, wherein the cholesterol lowering agent inhibits or reverses tendon xanthomata, thereby inhibiting or suppressing a tendinous or a musculoskeletal soft tissue injury in a subject.

In another embodiment, the present invention provides a method of ameliorating symptoms associated with a tendinous or a musculoskeletal soft tissue injury in a subject in need thereof, comprising the step of: administering to said subject a cholesterol lowering agent wherein said cholesterol lowering agent inhibits or reverses tendon xanthomata, thereby ameliorating symptoms associated with a tendinous or a musculoskeletal soft tissue injury in a subject.

In another embodiment, the present invention provides a method of accelerating the healing of a tendinous or a musculoskeletal soft tissue injury in a subject in need thereof, comprising the step of: administering to said subject a cholesterol lowering agent, wherein said cholesterol lowering agent inhibits or reverses tendon xanthomata, thereby accelerating the healing of a tendinous or a musculoskeletal soft tissue injury in a subject.

In another embodiment, the present invention provides a valid test based on the interaction of elevated cholesterol levels and tendon pathology. In another embodiment, the present invention provides a valid test based on the interaction of elevated cholesterol levels and tendon healing. In another embodiment, the present invention provides that tendon injuries comprise chronic degenerative changes.

In another embodiment, the present invention provides that hypercholesterolemia affects the biomechanical, histologic (organizational) and immunohistochemical properties of tendons. In another embodiment, the present invention provides that increased levels of cholesterol lead to reduced collagen organization within the tendon and inferior biomechanical properties.

In another embodiment, the present invention provides that hypercholesterolemia affects the mechanical and organizational properties of tendons. In another embodiment, the present invention provides that hypercholesterolemia affects the mechanical and organizational properties of tendons after injury. In another embodiment, the present invention provides that hypercholesterolemia causes hyper sensitivity to tendon injury. In another embodiment, the present invention provides that a subject afflicted with hypercholesterolemia has increased probability to develop a tendon injury. In another embodiment, the present invention provides that tendon injury can serve as a preliminary marker to hypercholesterolemia. In another embodiment, the present invention provides that a subject afflicted with tendon injury has increased probability to develop hypercholesterolemia.

In another embodiment, the present invention provides that alterations in cholesterol levels affect the mechanical properties of repairing tendon. In another embodiment, the present invention provides that elevated cholesterol levels affect the mechanical properties of repairing tendon. In another embodiment, the present invention provides that elevated cholesterol levels inhibit the mechanical properties of repairing tendon.

In another embodiment, the present invention provides that in tendons of hypercholesterolemic subject, the material properties (e.g., stress, modulus) are inferior to controls and remain so over time. In another embodiment, the present invention provides that in tendons of hypercholesterolemic subject, the structural mechanical properties (e.g., load, stiffness) approach normal over time due to an increase in cross-sectional area associated with increased fibrosis.

In another embodiment, the present invention provides that hypercholesterolemia affects the organizational properties of a musculoskeletal soft tissue. In another embodiment, the present invention provides that hypercholesterolemia affects the mechanical and organizational properties of a musculoskeletal soft tissue after injury. In another embodiment, the present invention provides that hypercholesterolemia causes hyper sensitivity to a musculoskeletal soft tissue injury. In another embodiment, the present invention provides that a subject afflicted with hypercholesterolemia has increased probability to develop a musculoskeletal soft tissue injury. In another embodiment, the present invention provides that a musculoskeletal soft tissue injury can serve as a preliminary marker to hypercholesterolemia. In another embodiment, the present invention provides that a subject afflicted with a musculoskeletal soft tissue injury has increased probability to develop hypercholesterolemia.

In another embodiment, the present invention provides that alterations in cholesterol levels affect the mechanical properties of repairing a musculoskeletal soft tissue injury. In another embodiment, the present invention provides that elevated cholesterol levels affect the mechanical properties of repairing musculoskeletal soft tissue injury. In another embodiment, the present invention provides that elevated cholesterol levels inhibit the mechanical properties of repairing a musculoskeletal soft tissue injury.

In another embodiment, the present invention provides that in musculoskeletal soft tissue injury of hypercholesterolemic subject, the material properties (e.g., stress, modulus) are inferior to controls and remain so over time. In another embodiment, the present invention provides that in musculoskeletal soft tissue injury of hypercholesterolemic subject, the structural mechanical properties (e.g., load, stiffness) approach normal over time due to an increase in cross-sectional area associated with increased fibrosis.

In another embodiment, the present invention provides that cholesterol lowering drugs reduce pain associated with musculoskeletal injuries. In another embodiment, the present invention provides that cholesterol lowering drugs inhibit healing of musculoskeletal soft tissue injuries. In another embodiment, the present invention provides that cholesterol lowering drugs would improve the ability to both treat and prevent musculoskeletal injuries and/or tendon injuries.

In another embodiment, the present invention provides that cholesterol lowering drugs improve revascularization problems associated with tendon ruptures. In another embodiment, the present invention provides that cholesterol lowering drugs inhibit degenerative changes associated with tendon ruptures.

In another embodiment, the present invention provides a method of preserving a biomechanical property of a tendon in a subject, comprising administering to a subject a cholesterol lowering agent, thereby preserving a biomechanical property of a tendon in a subject.

In another embodiment, the present invention provides that evaluation of mechanical parameters at various stages of tendon injury show that a low level of injury is characterized by changes in the tendon's elongation without compromise in the stiffness. In another embodiment, the present invention provides that the varying responses of elongation, stiffness and hysteresis at increasing levels of injury reflect the mechanistic changes that underlie the process by which the tendon degenerates from subrupture loads.

In another embodiment, the present invention provides a method of evaluating the risk of a subject developing a tendinous or a musculoskeletal soft tissue injury in a subject, comprising the steps of: obtaining a biological sample from a subject; analyzing the concentration of TC, HDL-C, LDL-C, TG or their combination; and comparing the concentration to a standard, whereby if the concentration of TC, HDL-C, LDL-C, TG or their combination is different than a pre-determined threshold, the subject is in high risk of developing a tendinous or a musculoskeletal soft tissue injury. In another embodiment, the present invention provides a method of evaluating the risk of a subject developing a tendinous or a musculoskeletal soft tissue injury in a subject, comprising the steps of: obtaining a biological sample from a subject; analyzing the concentration of TC, HDL-C, LDL-C, TG or their combination; and comparing the concentration to a standard, whereby if the concentration of TC, HDL-C, LDL-C, TG or their combination is higher than a pre-determined threshold, the subject is in high risk of developing a tendinous or a musculoskeletal soft tissue injury. In another embodiment, the present invention provides that the standard is taken from a subject or a pool of subject with a low risk of developing a tendinous or a musculoskeletal soft tissue injury. In another embodiment, the present invention provides that the standard is taken from a subject or a pool of subject with a high risk of developing a tendinous or a musculoskeletal soft tissue injury. In another embodiment, the present invention provides that the biological sample is blood, plasma, sera, saliva urine, tendon tissue, or any combination thereof.

In another embodiment, the present invention provides a kit for diagnosing the risk of a subject developing a tendinous or a musculoskeletal soft tissue injury in a subject, comprising reagents, packaging and instructions for analyzing the concentration of TC, HDL-C, LDL-C, TG or their combination in a biological sample of the subject. In another embodiment, the present invention provides that the instruction comprise a pre-determined threshold for the concentration of said TC, HDL-C, LDL-C, TG in the biological sample.

In another embodiment, the invention provides a method of improving a response to treatment of a tendinous or musculoskeletal soft tissue injury, in a subject, comprising administering to said subject a first agent and a second agent, wherein said first agent is a therapeutic molecule for treating said tendinous or musculoskeletal soft tissue injury and said second agent is a cholesterol lowering agent, wherein said cholesterol lowering agent inhibits or reverses tendon xanthomata, thereby treating a tendinous or musculoskeletal soft tissue injury in said subject. In one embodiment, the first and second agents are co-administered. In another embodiment, the first and second agents are administered separately at different times.

Examples of a therapeutic molecule for treating tendinous include, but are not limited to, non-steroidal anti-inflammatory drugs (NSAIDs) and cortisone. Examples of NSAIDs include, but are not limited to, salicylate such as acetylsalicylic acid, amoxiprin, benorylate, choline magnesium salicylate, diflunisal, ethenzamide, faislamine, methyl salicylate, magnesium salicylate, salicyl salicylate, and salicylamide; arylalkanoic acid such as diclofenac, aceclofenac, alclofenac, bromfenac, etodolac, indomethacin, nabumetone, oxametacin, proglumetacin, sulindac, and tolmetin; 2-Arylpropionic acid (profens) such as ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, and tiaprofenic acid, N-Arylanthranilic acid (fenamic acid) such as mefenamic acid, flufenamic acid, meclofenamic acid, and tolfenamic acid; pyrazolidine derivative such as phenylbutazone, ampyrone, azapropazone, clofezone, kebuzone, metamizole, mofebutazone, oxyphenbutazone, phenazone, and sulfinpyrazone; oxicam such as piroxicam, droxicam, lomoxicam, meloxicam, and tenoxicam; COX-2 inhibitor such as celecoxib, etoricoxib, lumiracoxib, parecoxib, rofecoxib, and valdecoxib; and sulphonanilide such as nimesulide; licofelone and an omega-3 fatty acid.

In another embodiment, the invention provides a pharmaceutical composition of treating a tendinous or musculoskeletal soft tissue injury, in a subject, comprising a therapeutically effective amount of a cholesterol lowering agent, wherein said therapeutically effective amount of said cholesterol lowering agent inhibits or reverses tendon xanthomata, thereby treating a tendinous or musculoskeletal soft tissue injury in said subject.

In one embodiment, the present invention relates to the use of an apoptosis-modifying compound and/or its analog, derivative, isomer, metabolite, pharmaceutically acceptable salt, pharmaceutical product, hydrate, N-oxide, or combinations thereof for treating, preventing, suppressing, inhibiting or reducing the incidence of an apoptosis-mediated disorder. Thus, in one embodiment, the methods of the present invention comprise administering an analog of the apoptosis-modifying compound. In another embodiment, the methods of the present invention comprise administering a derivative of the apoptosis-modifying compound. In another embodiment, the methods of the present invention comprise administering an isomer of the apoptosis-modifying compound. In another embodiment, the methods of the present invention comprise administering a metabolite of the apoptosis-modifying compound. In another embodiment, the methods of the present invention comprise administering a pharmaceutically acceptable salt of the apoptosis-modifying compound. In another embodiment, the methods of the present invention comprise administering a pharmaceutical product of the apoptosis-modifying compound. In another embodiment, the methods of the present invention comprise administering a hydrate of the apoptosis-modifying compound. In another embodiment, the methods of the present invention comprise administering an N-oxide of the apoptosis-modifying compound. In another embodiment, the methods of the present invention comprise administering any of a combination of an analog, derivative, isomer, metabolite, pharmaceutically acceptable salt, pharmaceutical product, hydrate or N-oxide of the apoptosis-modifying compound.

As used herein, "pharmaceutical composition" means a "therapeutically effective amount" of the active ingredient, e.g., the apoptosis-modifying compound, together with a pharmaceutically acceptable carrier or diluent. A "therapeutically effective amount" refers, in one embodiment, to that amount which provides a therapeutic effect for a given condition and administration regimen.

The pharmaceutical compositions of the invention can be administered to a subject by any method known to a person skilled in the art, such as parenterally, paracancerally, transmucosally, trans-dermally, intramuscularly, intravenously, intra-dermally, subcutaneously, intra-peritonealy, intra-ventricularly, intra-cranially, intra-vaginally or intra-tumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the apoptosis-modifying compounds are formulated in a capsule. In accordance with this embodiment, the compositions of the present invention may comprise inert carrier, diluent, or a hard gelating capsule.

Further, in another embodiment, the pharmaceutical compositions are administered by intravenous, intra-arterial, or intramuscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intramuscular administration.

Further, in another embodiment, the pharmaceutical compositions are administered topically to body surfaces and are thus formulated in a form suitable for topical administration. Suitable topical formulations include gels, ointments, creams, lotions, drops and the like. For topical administration, the apoptosis-modifying compound agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of apoptosis-modifying compound agent over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof. Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled-release compositions, i.e. compositions in which the apoptosis-modifying compound is released over a period of time after administration. Controlled- or sustained-release compositions include formulation in lipophilic depots (e.g. fatty acids, waxes, oils). In another embodiment, the composition is an immediate-release composition, i.e. a composition in which all of the apoptosis-modifying compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled-release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the apoptosis-modifying compound agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the apoptosis-modifying compound agents or their physiologically tolerated derivatives such as salts, esters, N-oxides, and the like are converted into a solution, suspension, or emulsion, if desired with the substances customary and suitable for this purpose, for example, solubilizers or other substances.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, the compositions of the invention are administered in conjunction with other therapeutic agents. In another embodiment, the compositions of the invention are administered in conjunction with surgery or other therapy, to a patient who has a tendinous injury or a risk of developing tendinous injury.

In one example, the compositions of the present invention are administered to a patient in conjunction with a non-steroidal anti-inflammatory drug (NSAID). In another example, the compositions of the present invention are administered to a patient in conjunction with a cortisone drug. The compositions of the present invention may be administered in combination with one or more other prophylactic or therapeutic agents, including but not limited to cytotoxic agents, chemotherapeutic agents, cytokines, growth inhibitory agents, antihormonal agents, kinase inhibitors, cardioprotectants, immunostimulatory agents, immunosuppressive agents, agents that promote proliferation of tendinous or musculoskeletal soft tissue cells, protein tyrosine kinase (PTK) inhibitors, antibodies, or other therapeutic agents. In a particular embodiment, the methods of the present invention comprise administering a statin in combination with one or more therapeutic agents.

The compositions of the invention may include a "therapeutically effective amount" of an agent of the invention. A "therapeutically effective amount" refers to an amount effective, at dosages and for periods of time necessary, to achieve the desired therapeutic result. A therapeutically effective amount may vary according to factors such as the disease state, age, sex, and weight of the individual, and the ability of the agent to elicit a desired response in the individual. A therapeutically effective amount is also one in which any toxic or detrimental effects of the agent are outweighed by the therapeutically beneficial effects.

Dosage regimens may be adjusted to provide the optimum desired response. For example, a single dose may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of an agent calculated to produce the desired therapeutic effect in association with the required pharmaceutical carrier. For any particular patient or subject, specific dosage regimens may be adjusted over time according to the individual need and the professional judgment of the person administering or supervising the administration of the compositions.

EXAMPLES

Experimental Details

Animals

A total of 40 male B6.129P2-ApoetmlUnc/J (control mouse for this is C57BL/6J) hypercholesterolemia mice and 40 male control mice C57BL/6J are obtained from Jackson Laboratories and cared for at the animal facilities of the University of Pennsylvania's University Laboratory Animal Resources facility.

Description of Overall Experiments

The purpose of the first experiment is to determine the biomechanical, histologic (organizational) and Immunohistochemical properties of the uninjured patellar tendon in an environment of hypercholesterolemia. Mice are sacrificed at 13 weeks of age. Subsequently immunohistochemistry, histology, and biomechanics aspects are assessed.

The purpose of the second experiment is to determine the biomechanical, histologic (organizational) and immunohistochemical properties of the healing tendon in an environment of hypercholesterolemia. From this group, four mice are sacrificed 5 days post-surgery for the immunohistochemistry study, while four mice are sacrificed at 3 weeks post-surgery (13 weeks of age) for the histologic study and the remaining ten mice are sacrificed at 3 weeks post-surgery for the biomechanical study. For the experimental group, 18 mice are used.

Five days post-injury has been chosen for the immunohistochemistry assay based on the fact that cytokine expression occurs during the first (inflammatory) phase of tendon healing. It has also been a time point used for immunohistochemistry in previous studies utilizing this patellar tendon injury model. Three weeks post-injury has been chosen for histologic (organizational) and biomechanical study since by three weeks post-injury, a balance between collagen synthesis and breakdown has been reached and remodeling has begun.

Specimen Size Justification

Based on previous mouse patellar tendon biomechanical properties, the normal variation in measurement parameters to be utilized for power calculations has been estimated. These data were obtained through biomechanical tests of mouse patellar tendons in this laboratory following the same protocols as those to be used in the current proposal. To detect a moderate effect size of 1.2 at 80% power, 10 animals per group are needed (p<0.05). In recognition that multiple measures are observed for each tendon in each group, a Bonferroni correction for multiple comparisons are performed appropriately. Based on a similar calculation and given the expected variation in the angular deviation in measuring collagen organization (a measure of fiber distribution spread) from previous mouse patellar tendon experiments, four animals per group are needed.

Numbers of animals for other assays are sufficient to provide more qualitative information (no statistical evaluation to be performed). This information is expected to be supportive and to help explain the difference in the quantitative results. This information is also be useful for proposing potential mechanisms of alterations for future investigation.

Surgical Injury Model

The patellar tendon is injured in both legs of each mouse as detailed under the description of experiments section of this proposal.

For the surgical procedure, mice are administered buprenorphine as a pre-(0.1 mg/kg) and post-(0.5 mg/kg) operative analgesia. In preparation for the surgical procedure, mice are anesthetized with a mixture of isoflurane and oxygen, and both hindlimbs are shaved. The mice are placed in a supine position with the knee flexed. A skin incision medial to the knee is made and the skin pulled aside to expose the patellar tendon. Two cuts parallel to the tendon are made in the retinaculum on each side, and a plastic-coated blade is placed underneath the patellar tendon. With the coated blade serving as support, a 0.75 mm diameter biopsy punch (Shoney Scientific, Waukesha, Wis.) is used to create a full-thickness partial transection in the patellar tendon (see FIG. 3). The plastic backing is removed, leaving a distinct and reproducible injury.

Histological Evaluation

The histological and organizational testing follow previously established protocols developed in our laboratory. Four mice from the experimental groups are designated for histological and organizational analysis, and the patellar tendons is immediately dissected following sacrifice. The tendons are dissected free from the patella and tibia, processed with standard histological techniques and embedded in paraffin blocks. 7 μM cut parallel to the tendon fibers, and stained with H&E.

A qualitative analysis of the tissue slides is performed using light microscopy to assess the presence of foam cells and collagen fiber organization. This analysis is performed by assigning a rank to each of the observations where 0 indicates normal, 1 indicates mild changes, 2 indicates moderate changes, and 3 indicates marked changes. Standard images representing each grading level for each measure is prepared to provide consistency across graders. The histological analysis is performed independently and blindly by three graders on representative sections from each of these tendons. For each variable examined, measures from the three graders are averaged, yielding an overall histological grade for the tissue sections. This methodology has been used previously in our laboratory for histological tissue assessment.

The slides are also analyzed using a quantitative polarized light microscopy method developed in our lab. Grayscale images of the tendon are taken at 5° increments with crossed analyzer and polarizer simultaneously rotated through 90°. Subsequently, the filter is removed and images taken again at 5° C. increments while a X compensator is rotated through 90° along with crossed analyzer and polarizer. Custom-designed software is then be utilized to determine collagen fiber orientations. This program allows the user to define the area of interest and the number of points within that area to be analyzed. Next, a graph of light intensity versus section orientation for each of the points is plotted. Extinction angles for each point are visually inspected, and points that do not follow a typical plot, as would be the case if the point were located on an empty space, are deleted. The average angle is then defined to be 90° C. for the purpose of statistical analysis.

Using a circular statistics package (Oriana version 1.06), collagen fiber distributions is statistically compared using a Chi-Squared method to test goodness of fit. To determine where the differences lie between samples, the angular deviation (AD) of the collagen orientations, a measure of fiber distribution spread, is also calculated. r is the length of the mean vector. This r value ranges from 0 to 1, with the larger numbers indicating that the observations are clustered more closely around the mean than lower numbers.

Immunohistochemical Evaluation

For the immunofluorescence analysis, the patellar tendons are immediately dissected following sacrifice. Similar to the organizational study, the tendons are also dissected free from the patella and tibia, processed, embedded in paraffin, and sectioned. The methods for immunohistochemical analysis include the following: tendons are embedded in paraffin. Serial sections (8 μm) of tissue are mounted on masked 10-well slides. Sections are fixed in acetone, air-dried and rehydrated in PBS containing 0.02% $NaN_3$, and blocked with 1% BSA in $PBS/NaN_3$. For detection of specific antigens, sections are reacted with the appropriate antibody followed by incubation with biotinylated anti-IgG antibody against the appropriate species, or reacted with biotinylated binding protein. Immunostaining is photographed on a Leica microscope using a Nikon 2020 or digitally captured.

The biomechanical testing follow previously established protocols. Ten mice from the experimental group are designated for geometric and biomechanical analysis. On the day of testing, specimens are thawed at room temperature before dissection. First, the entire left hindlimb is dissected free by severing the femur. This hindlimb is then be cleaned, leaving only the patella, patellar tendon, and tibia as one connected unit. The central area of interest in the patellar tendon is prepared as a standardized dumbbell-shaped specimen. A 0.1-mm thick double-edged razor blade is cut in half and each half bent within a custom device to create a consistent dumbbell-shaped stamp. Subsequently, two Verhoeff stain lines are placed on either end of the dumbbell shape on the tendon to serve as a gauge section for optical strain analysis. Next, the tendon width and thickness are quantified, and cross-sectional area calculated as the product of the two. Tendon width is measured using an optically based image processing system, and tendon thickness is quantified by lowering a fine indenter probe attached to a high-resolution linear variable differential transformer. After determining tendon width and thickness, the tibia is embedded in polymethylmethacrylate and secured in place with a metal pin. The potted specimen is then placed in PBS until testing, to be performed on the same day.

Figure 4:
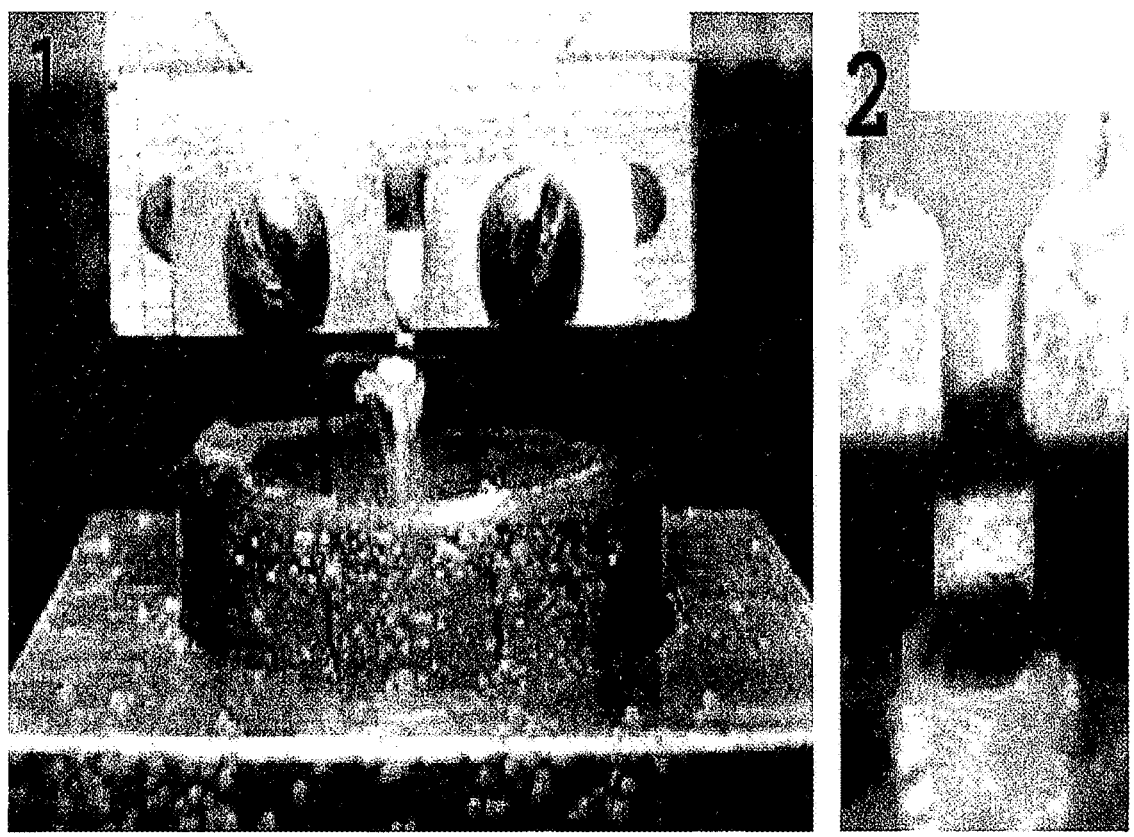
FIG. 4 is a photograph showing a patellar tendon placed in custom fixtures for mechanical testing.

The patella is held in place with a custom-designed cone-shaped wedge fixture, and the potted tibia end is secured to a custom-designed base (FIG. 4).

Each tendon specimen undergoes the following standard protocol: while immersed in a 37° C. saline bath—preloaded to 0.02 N at a rate of 0.1%/s (0.003 mm/s), preconditioned for 10 cycles from 0.02 to 0.04 N at a rate of 0.1%/s (0.003 mm/s), and held for 300 s. Immediately following this preconditioning, a stress-relaxation experiment is performed by elongating the tendon to a strain of 5% (0.15 mm) at a rate of 25%/s (0.75 mm/s), followed by a relaxation for 600 s. Finally, a ramp to failure is applied at a rate of 0.1%/s (0.003 mm/s). A custom written program in Labview is used to capture images during the test. Using the stain lines from these images, local tissue strain is measured optically.

Measures of elastic properties, stiffness and modulus are calculated using linear regression from the linear region of the load-displacement and stress-strain curves, respectively. Measures of viscoelastic properties, peak and equilibrium load and stress is determined from the stress relaxation curve. From these, the load ratio is calculated as the ratio of the equilibrium load to peak load values. As a method for further assessing the properties of the tendon, Fung's Quasilinear Viscoelastic (QLV) Model is be 2)T1, and used to extract additional elastic (A and B) and viscous (C, parameters from the stress-relaxation experiment. These parameters are determined by curve-fitting data from the stress-relaxation portion of the protocol to the mathematical model as proposed by Fung with modifications to account for the finite ramp. Statistical analysis is performed using the student's t-test to compare between the control and experimental groups and =0.05.ausing the SYSTAT software package.

Example 1

The Effects of Hypercholesterolemia on Rotator Cuff Disease

Cholesterol data was collected on an age matched population of 240 patients: 120 of these patients (mean age 66.7) had ruptures of their rotator cuff tendons, while the control group consisted of 120 patients (mean age 65.4) seen in the orthopedic clinic for non-tendon related shoulder complaints. Total cholesterol (TC) and low-density lipoprotein cholesterol (LDL-C) concentrations of the patients with rotator cuff tendon tears were higher ($p<0.05$). 68% of the patients with rotator cuff tears had an elevated serum cholesterol, as compared to an overall rate of 24% in our control group. Using Hill's criteria for causality it was found that in patients with rotator cuff tears there was a positive correlation between mixed hyperlipidemia and rotator cuff tears.

This shows that the measurement of serum cholesterol in patients presenting with torn tendons provides with an opportunity to treat patients with hypercholesterolemia who otherwise may have gone undiagnosed and undertreated for years. This provides the opportunity to identify patients with hypercholesterolemia earlier and prevent the onset of such problems as future tendon ruptures, myocardial infarction, peripheral vascular disease, and cerebrovascular accidents. Future consideration of drug treatment specifically statin drugs may reduce the risk for future tendon degeneration, improve quality of life, decrease the risk of repair failure, and reduce morbidity and mortality.

Example 2

Injury Model

Figure 2:
FIG. 2 is a photograph showing the defect on the patellar tendon after injury.

The patellar tendon model of the C57BL/6 mouse is a consistent and reproducible model of tendon injury with which this laboratory has extensive experience. The patellar tendon width in this particular mouse is 1.25 mm. The injury itself involved using a 0.75 mm diameter punch in the central portion of the tendon. With this partial-width transection, the marginal fibers in the periphery of the tendon would be left intact to allow for immediate post-operative tendon mobilization. These marginal fibers also circumvent the need for sutures, which can have harmful effects on the healing process and also eliminate the variability seen with surgical repair (FIGS. 1 and 2).

Figure 3:
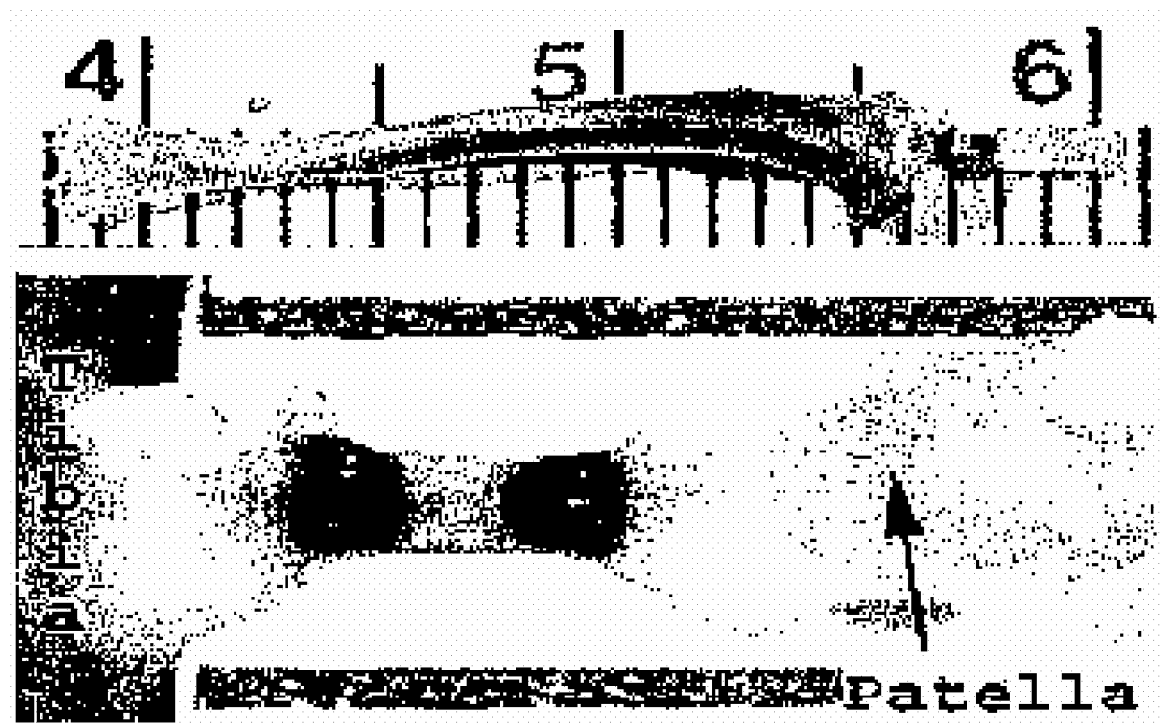
FIG. 3 shows a testing unit comprised of patella, patellar tendon, and tibia (top). Magnified picture of dumbbell-shape stamped patellar tendon with Verhoeff stain lines (bottom). Ruler in both pictures is in millimeters.

The superficial position of the mouse patellar tendon allows for easy identification and is also conducive to the delivery of agents to the patellar tendon that can modulate healing. Using the 0.75 mm diameter punch described above (60% of tendon width), a full thickness transection was created in the middle of the left patellar tendon with the right tendon undergoing a sham surgery. Details of this injury model are provided in the Methods and Materials section. For the organizational assay, tendons were processed with standard techniques (H&E stain) and viewed under polarized light (FIG. 3).

For biomechanical testing, each tendon specimen underwent preconditioning, a stress-relaxation experiment and a test to failure in a body temperature PBS bath.

Example 3

The Impact of Increased Serum Cholesterol

The increased serum cholesterol in the experimental group, leads to inferior collagen organization and thus worse biomechanical properties in the adult mouse tendon as compared to the control group. These significant findings prove the interaction of hypercholesterolemia and rotator cuff disease.

Example 4

Hypercholesterolemia is Detrimental to Tendon Properties and Healing in a Mouse Injury Model The objective of the present study was to evaluate tendon healing in normal and hypercholesterolemic mice at an advanced age using a patellar tendon injury model. The inventors of the instant application demonstrated that tendons from aging hypercholesterolemic mice exhibits inferior baseline mechanical properties and tendon healing compared to normal controls.

Twenty-four male C57BL/6 control mice (CTL) and 24 male C57BL/6 mice deficient for Apolipoprotein E (APOE) representing a hypercholesterolemia group were obtained (IACUC approved). These APOE mice have markedly elevated total plasma cholesterol levels as well as reduced high-density lipoprotein (HDL)-to-LDL ratios. For each group, ten animals were sacrificed without injury to provide baseline, uninjured data. Patellar tendons from the remaining 28 animals were injured. Briefly, incisions were made in the retinaculum adjacent to the tendon. A 0.75 mm diameter biopsy punch was used to create a full thickness, central (~60% width) defect in the left limb. The use of a central defect prevented the need for suture repair of the tendon. The right limb underwent a sham surgery, which included all procedures except for the defect itself. Skin incisions were closed and mice were allowed normal cage activity. Animals were sacrificed at 43 weeks of age (3 weeks post-injury for operated animals).

For biomechanical evaluation, patellar tendons (n=7-10 per group) were dissected, leaving the patella-tendon-tibia complex intact. Tendon cross-sectional area was measured using a custom laser-based device. The tendon was then stamped into a dumbbell shape and cross-sectional area was again measured for use in calculation of material properties. The tibia was potted in PMMA and placed in custom fixtures. Specimens were submerged in a 37° C. PBS bath and tensile tested as follows: preload, preconditioning, stress relaxation for 10 minutes at 5% strain, return to gage length, and ramp to failure (0.1%/s). Tissue strain was measured optically.

Data were evaluated for differences in baseline and in healing between groups. For healing assessment, data from the injured limbs were normalized to that of the sham-operated contralateral limbs. Comparisons between CTL and APOE tendons were made using a one-tailed unpaired t-test for significance ($p \leq 0.05$) and trends ($0.05 < p \leq 0.1$).

Figure 5:
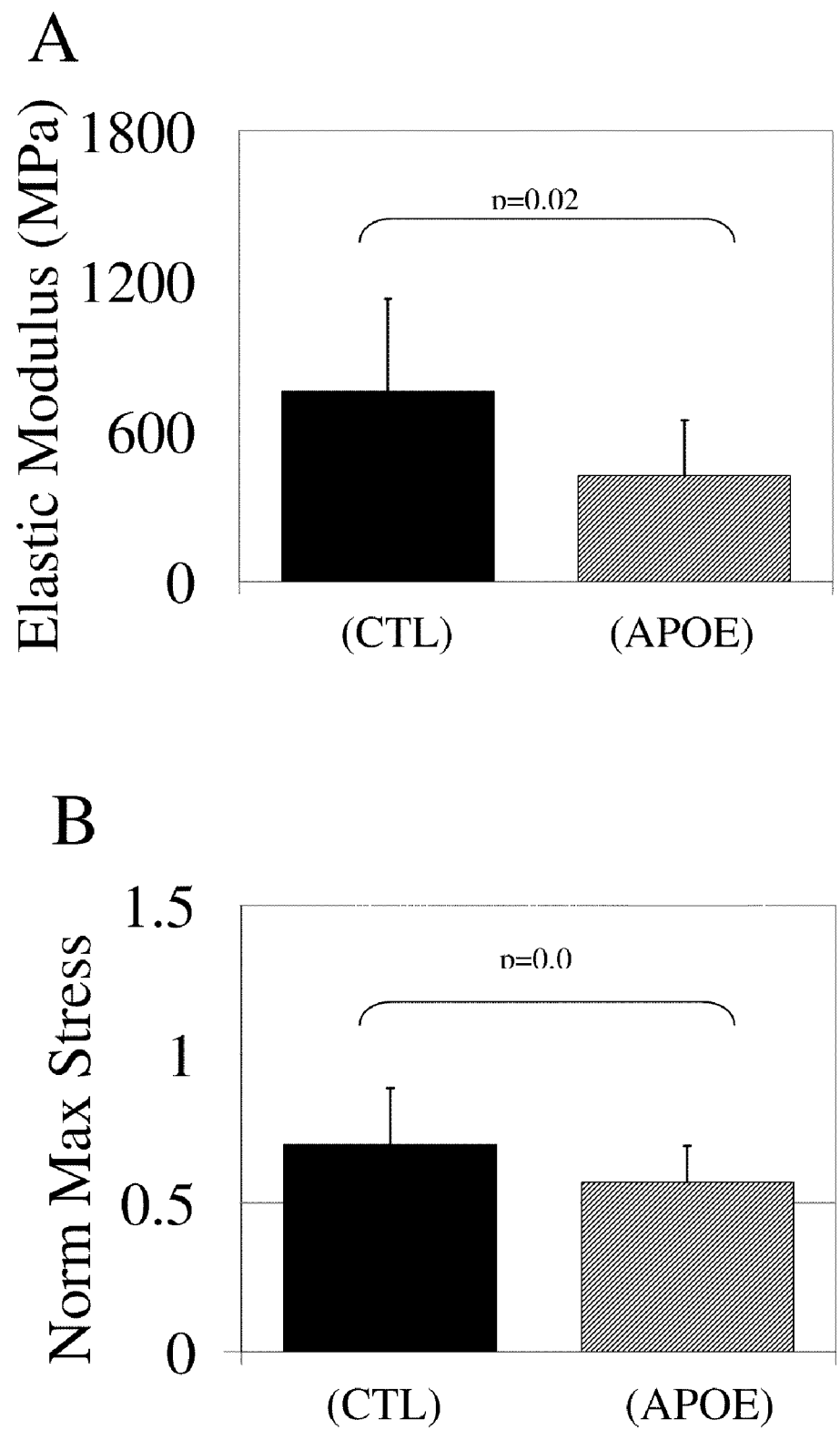
FIG. 5 shows (a) Elastic modulus of APOE uninjured tendons was significantly reduced compared to CTL; and (b) Normalized maximum stress in injured tendons recovered significantly closer to baseline (value of 1.0) for CTL mice.

Uninjured patellar tendons from APOE mice showed a significant decrease in elastic modulus (Table 1, FIG. 5A, p=0.02) and a trend toward increased cross-sectional area (Table 1, p=0.1) compared to control. For injured data, properties are presented as normalized ratios (injured/sham). Normalized maximum stress was significantly lower in the APOE group than in the controls (Table 1, FIG. 5B, p=0.05) and there were no differences in normalized area or modulus.

TABLE 1

Results from uninjured and normalized (injured/sham) paired tendons.

| | Uninjured Area (mm$^2$) | Uninjured Modulus (MPa) | Normalized Max Stress |
|---|---|---|---|
| CTL | 0.25 (0.05) | 759.6 (370.7) | 0.70 (0.19) |
| APOE | 0.28 (0.07) | 423.1 (220.1) | 0.57 (0.12) |
| p-value | 0.1[#] | 0.02[*] | 0.05[*] |

Data are presented are means (±SD).
p-values are denoted as [*]significant or [#]trends between CTL and APOE groups.

Healing was assessed in patellar tendons from normal (CTL) and hypercholesterolemic (APOE) mice. As hypothesized, APOE tendons exhibited reduced healing strength and baseline elastic modulus compared to controls.

The present results are contrary to the previous finding of improved healing strength in APOE tendons. As noted, the mice in the current study were appreciably older than in the previous study. The reduction in tendon healing in aging hypercholesterolemic tendons can be linked to the cumulative effects of intratendinous cholesterol deposition or relative tissue ischemia due to vascular compromise, as seen clinically in older patients. In summary, the inventors of the instant application have demonstrated reduced modulus and healing strength in hypercholesterolemic mice.

Example 5

High Cholesterol Adversely Affects Biceps Tendon Mechanical Properties in a Porcine Model The objective of this study was to investigate potential relationships between high cholesterol and shoulder tendon mechanics in an existing porcine model. The inventors of the instant application found that biceps tendons from hypercholesterolemic pigs have reduced mechanical properties when compared to those of normal controls.

A total of seven male Yorkshire pigs (103 kg average) were used in this IACUC-approved study. At 3-4 months of age, a control group (n=3) continued to receive a normal diet while a high cholesterol group (n=4) received a diet of 0.5% cholesterol, 10% lard, and 1.5% sodium cholate for a period of five months. At the end of the five month treatment, all animals were sacrificed. Biceps tendons were dissected from the right shoulder of each animal and prepared for biomechanical testing as described below.

Figure 6:
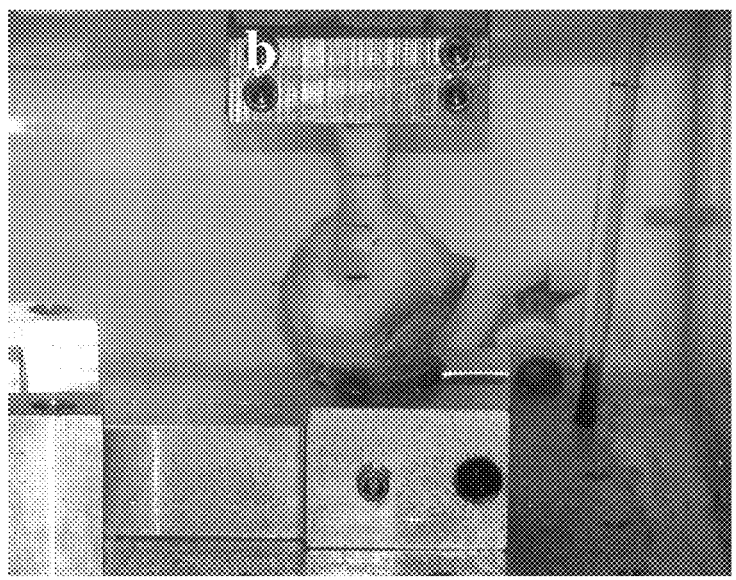
FIG. 6 shows (a) Pig biceps tendon placed in test fixture, submerged in PBS bath at body temperature; and (b) shown during tensile testing.
Figure 6:
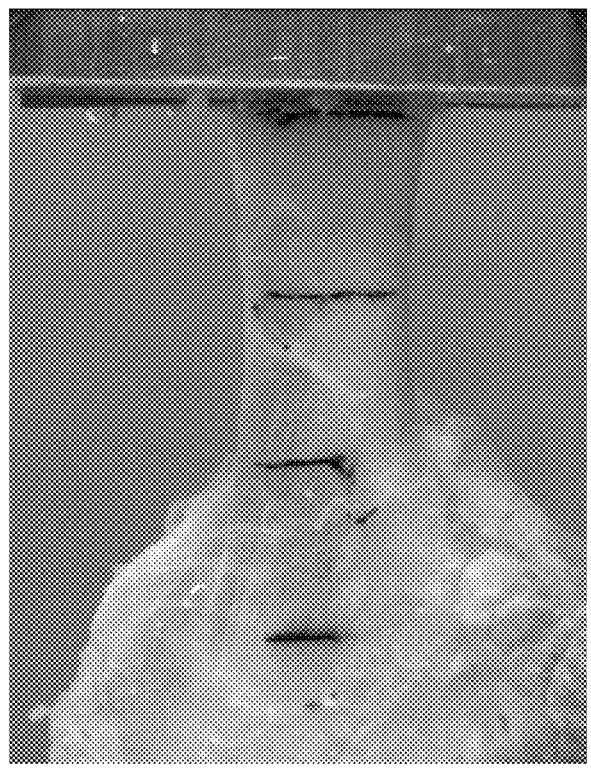

Biceps tendons were dissected free from the muscle insertion, while leaving the bony insertion intact. The glenoid was then separated from the scapula using a pneumatic saw. To facilitate calculation of optical strain, three stain lines were placed on the tendon—one at the insertion above the glenoid and two others in the tendon midsubstance (FIG. 6), leaving a total gauge length of 30 mm. Tendon cross-sectional area was measured using a custom laser-based device. The distal end of the biceps was fixed between two layers of sandpaper using a cyanoacrylate adhesive and clamped using custom serrated grips. The remaining portion of the scapula/glenoid was then potted in PMMA and placed in a base fixture (FIG. 6). Specimens were submerged in a 37° C. PBS bath and tensile tested as follows: preload, preconditioning, and ramp to failure at 0.1%/s. Data between groups were evaluated using a one-tailed unpaired t-test with significance set at $p \leq 0.05$.

Mean cholesterol levels at the time of sacrifice were 290 mg/dL for the hypercholesterolemic (HC) group and under 100 mg/dL for the control (CTL) group (no quantitative measure below 100 was recorded).

Figure 7:
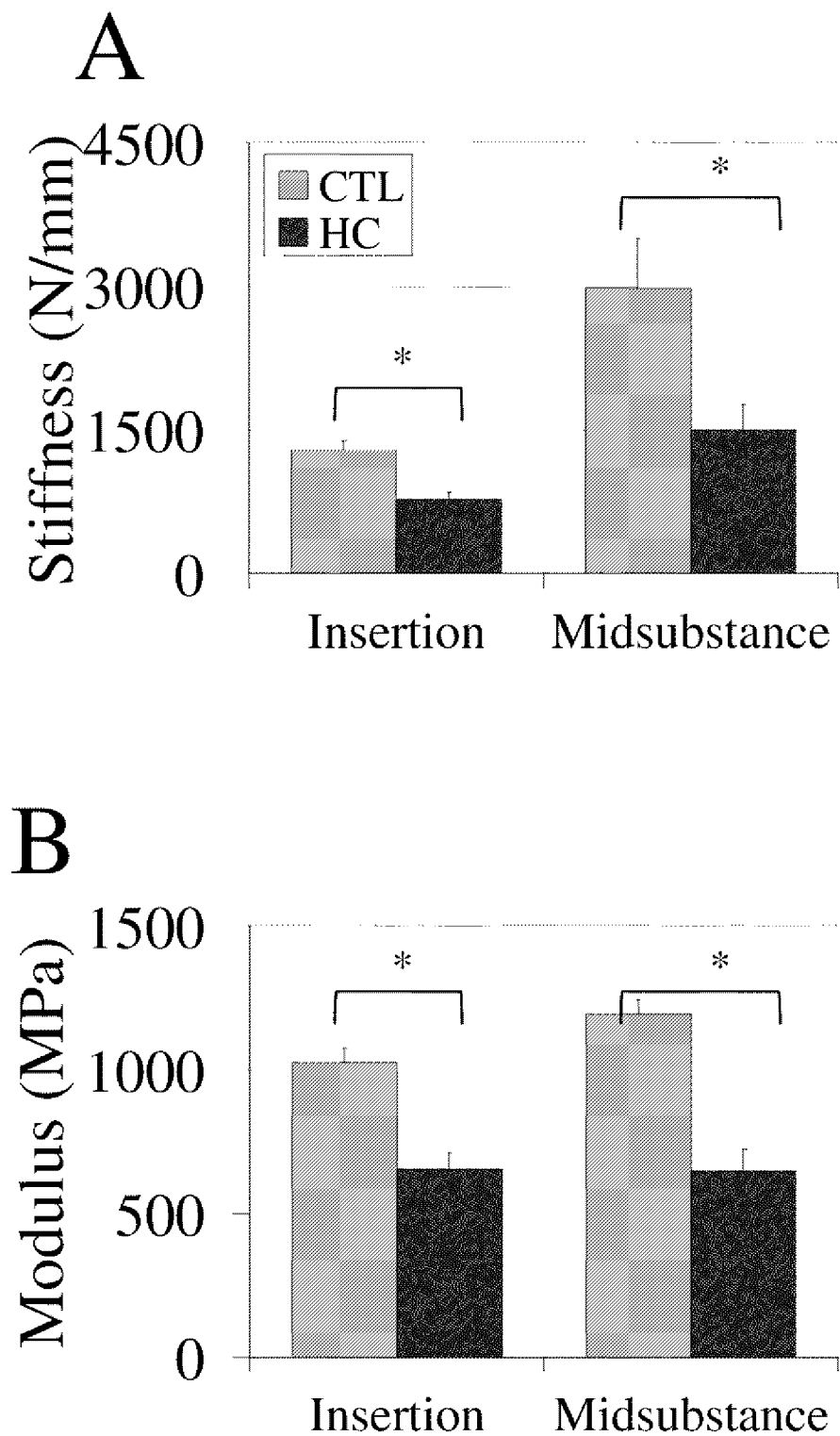
FIG. 7 shows that Stiffness and modulus were significantly reduced (*) in the high cholesterol (HC) tendons compared to control (CTL) both at the insertion site and in the tendon midsubstance.

No differences were noted in tendon size as measured by cross-sectional area (Table 2). Biomechanical testing revealed significantly reduced stiffness ($p \leq 0.002$) and Young's modulus ($p \leq 0.0001$) in the HC group compared to CTL tendons (Table 2, FIG. 7). This finding was present for both tendon midsubstance and insertion site properties.

It was shown that tendons from hypercholesterolemic pigs would demonstrate inferior properties compared to normal control tendons. Mechanical testing demonstrated that biceps tendons of hypercholesterolemic animals were severely compromised compared to those of control animals. This is the first study reporting effects of hypercholesterolemia on native tendon mechanical properties. The present finding of substantially reduced mechanics supports our clinical observations relating high cholesterol and the incidence of tendon tears.

In this study, the inventors of the instant application have shown a detrimental effect of high cholesterol on normal tendon mechanics in the pig shoulder. While this study includes only a small sample size, the particularly low variance in the data and striking nature of the statistically significant results provide strong confidence in the findings.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating a tendinous or musculoskeletal soft tissue injury, in a subject with hypercholesterolemia, comprising systemically administering to said subject with hypercholesterolemia a therapeutically effective amount of a cholesterol lowering agent, wherein said soft tissue injury is a patellar tendon injury, thereby treating said soft tissue injury in said subject.

2. The method of claim 1, wherein said cholesterol lowering agent is a statin drug, and wherein the statin drug comprises atorvastatin.

3. The method of claim 1, wherein said cholesterol lowering agent lowers said subject's blood total cholesterol concentration below about 240 mg/dL.

4. The method of claim 1, wherein said cholesterol lowering agent lowers said subject's blood LDL-C to below about 130 mg/DL.

5. The method of claim 1, wherein said cholesterol lowering agent raises said subject's blood HDL-C to about 40 mg/DL.

6. The method of claim 1, wherein said cholesterol lowering agent lowers said subject's blood TG to below about 150 mg/DL.

7. The method of claim 1, further comprising treating inflammation associated with said tendinous or musculoskeletal soft tissue injury.

8. The method of claim 1, further comprising treating edema associated with said tendinous or musculoskeletal soft tissue injury.

TABLE 1

Tensile testing data of pig biceps tendons.

|  | Area (mm$^2$) | Insert. Stiffness (N/mm) | Midsub. Stiffness (N/mm) | Insert. Modulus (MPa) | Midsub. Modulus (MPa) |
|---|---|---|---|---|---|
| CTL | 25.9 (2.29) | 1289.0 (101.6) | 2976.9 (518.9) | 1024.3 (51.6) | 1194.2 (50.9) |
| HC | 24.2 (4.00) | 769.9 (82.9) | 1497.9 (261.7) | 656.5 (53.8) | 647.4 (76.2) |
| p-value | 0.3 | 0.0003* | 0.002* | 0.0001* | 0.00006* |

Data are presented as means (±SD).
*denotes statistical significance between control (CTL) and high cholesterol (HC) groups.

9. A method of inhibiting or suppressing a tendinous or musculoskeletal soft tissue injury in a subject with hypercholesterolemia, comprising systemically administering to said subject with hypercholesterolemia a therapeutically effective amount of a cholesterol lowering agent, wherein said soft tissue injury is a patellar tendon injury, thereby inhibiting or suppressing said soft tissue injury in said subject.

10. A method of ameliorating symptoms associated with a tendinous or musculoskeletal soft tissue injury, in a subject with hypercholesterolemia, comprising systemically administering to said subject with hypercholesterolemia a therapeutically effective amount of a cholesterol lowering agent wherein said soft tissue injury is a patellar tendon injury, thereby ameliorating symptoms associated with said soft tissue injury in said subject.

11. A method of accelerating the healing of a tendinous or musculoskeletal soft tissue injury, in a subject with hypercholesterolemia, comprising systemically administering to said subject with hypercholesterolemia a therapeutically effective amount of a cholesterol lowering agent, wherein said soft tissue injury is a patellar tendon injury, thereby accelerating the healing of said soft tissue injury in said subject.

12. A method of evaluating the risk of developing a patellar tendon injury, in a subject, comprising the steps of: obtaining a biological sample from said subject; determining the concentration of TC, HDL-C, LDL-C, TG or their combination in said sample; and comparing the concentration in said sample to a standard that comprises the concentrations of TC at 240 mg/DL, HDL-C at 40 mg/DL, LDL-C at 130 mg/DL, and TG at 150 mg/DL; analyzing differences in the concentrations between said sample and said standard, whereby if the concentration of TC, LDL-C, TG or their combination in said sample is higher or the concentration of HDL-C is lower than the corresponding concentration of said standard, the subject is in high risk of developing said injury.

* * * * *